(12) United States Patent
Jiang et al.

(10) Patent No.: US 10,595,741 B2
(45) Date of Patent: Mar. 24, 2020

(54) METHOD AND SYSTEM FOR BRAIN ACTIVITY DETECTION

(71) Applicant: Institute of Automation Chinese Academy of Sciences, Beijing (CN)

(72) Inventors: Tianzi Jiang, Beijing (CN); Xin Zhang, Beijing (CN); Nianming Zuo, Beijing (CN); Juanning Si, Beijing (CN); Ruirui Zhao, Beijing (CN); Jian Yu, Beijing (CN)

(73) Assignee: Institute of Automation Chinese Academy of Sciences, Beijing (CN)

( * ) Notice: Subject to any disclaimer, the term of this patent is extended or adjusted under 35 U.S.C. 154(b) by 344 days.

(21) Appl. No.: 15/501,978

(22) PCT Filed: Aug. 6, 2014

(86) PCT No.: PCT/CN2014/083802
§ 371 (c)(1),
(2) Date: Feb. 6, 2017

(87) PCT Pub. No.: WO2016/019526
PCT Pub. Date: Feb. 11, 2016

(65) Prior Publication Data
US 2017/0224246 A1 Aug. 10, 2017

(51) Int. Cl.
*A61B 5/00* (2006.01)
*A61B 5/0478* (2006.01)
(Continued)

(52) U.S. Cl.
CPC .......... *A61B 5/0478* (2013.01); *A61B 5/0476* (2013.01); *A61B 5/14542* (2013.01);
(Continued)

(58) Field of Classification Search
CPC combination set(s) only.
See application file for complete search history.

(56) References Cited

U.S. PATENT DOCUMENTS

| 6,516,214 | B1 * | 2/2003 | Boas | A61B 5/0073 600/310 |
|---|---|---|---|---|
| 8,103,328 | B2 * | 1/2012 | Turner | A61B 5/0478 600/383 |

(Continued)

FOREIGN PATENT DOCUMENTS

| CN | 101853070 A | 10/2010 |
|---|---|---|
| CN | 102156541 A | 8/2011 |

(Continued)

OTHER PUBLICATIONS

PCT/CN2014/083802 International Search Report.

*Primary Examiner* — Michael W Kahelin
*Assistant Examiner* — Shirley X Jian
(74) *Attorney, Agent, or Firm* — Maier & Maier, PLLC

(57) ABSTRACT

A method and system for detecting brain activity may be disclosed, the method including performing multi-channel synchronous collections of brain electrical signals and cerebral cortex blood oxygen signals simultaneously and ensuring synchronicity of the collected signals among channels by collecting the signals at multiple locations simultaneously. A system may include a functional near-infrared light source emission module, which may employ the frequency division multiplexing technique. A multi-functional joint collection helmet may access the light source signal emitted from the emission module, then may be processed by a near-infrared detection module. Further, the near-infrared detection module may detect optical signals of the scalp, while a brain electricity detection module detects electrical signals of the scalp. Finally, a central control unit may synchronize data collected from the detected signals and may control a variety of functional modules and upload the data to a host computer.

6 Claims, 5 Drawing Sheets

(51) Int. Cl.
*A61B 5/0476* (2006.01)
*A61B 5/1455* (2006.01)
*A61B 5/145* (2006.01)

(52) U.S. Cl.
CPC ........ *A61B 5/14553* (2013.01); *A61B 5/6803* (2013.01); *A61B 5/7203* (2013.01); *A61B 5/725* (2013.01); *A61B 5/7225* (2013.01); *A61B 5/7246* (2013.01); *A61B 2562/066* (2013.01)

(56) References Cited

U.S. PATENT DOCUMENTS

| | | | | |
|---|---|---|---|---|
| 8,396,525 | B2 * | 3/2013 | Ishikawa | A61B 5/14553 600/310 |
| 8,821,397 | B2 * | 9/2014 | Al-Ali | A61B 5/0006 600/301 |
| 9,579,061 | B2 * | 2/2017 | Udagawa | A61B 5/0059 |
| 2009/0318785 | A1 | 12/2009 | Ishikawa | |
| 2010/0292569 | A1 * | 11/2010 | Hielscher | A61B 5/0073 600/425 |
| 2016/0103487 | A1 * | 4/2016 | Crawford | G06F 3/015 600/544 |
| 2016/0143541 | A1 * | 5/2016 | He | A61B 5/0093 600/409 |
| 2017/0258390 | A1 * | 9/2017 | Howard | A61B 5/16 |
| 2017/0281014 | A1 * | 10/2017 | von Luehmann | A61B 5/4064 |
| 2017/0311803 | A1 * | 11/2017 | Hirsch | A61B 5/4836 |
| 2019/0159675 | A1 * | 5/2019 | Sengupta | A61B 5/0476 |

FOREIGN PATENT DOCUMENTS

| | | |
|---|---|---|
| CN | 202161317 U | 3/2012 |
| CN | 102894971 A | 1/2013 |
| CN | 103445774 A | 12/2013 |
| WO | 2009104644 A1 | 8/2009 |

\* cited by examiner

METHOD AND SYSTEM FOR BRAIN ACTIVITY DETECTION

TECHNICAL FIELD

The present invention relates to a method and a system for brain activity detection, in particular to an integrated collection system that collects electrical activities of brain neurons based on the EEG technology and that synchronously collects changes in blood oxygen metabolism in corresponding brain areas at the same time through the functional near-infrared technology.

BACKGROUND OF THE INVENTION

Brain functional activities include several procedures like neuronal activity and local energy metabolism, and complicated functional activities enable the brain to bring together information of multiple modes, among which electrical activities of neurons and changes in blood oxygen metabolism in active areas are the most important, and only by effectively extracting, analyzing and combining said two kinds of information, can the brain functional activities be organically linked to each other. Currently, combining the nerve electrophysiological equipment and the metabolic process detection equipment to make full use of the advantages thereof has become an important means for deeply detecting and understanding neural information.

The system intends to realize integration of the three functions of near-infrared spectrometer, electroencephalograph and fusion device of near-infrared spectrum and electroencephalograph on one instrument through an effective combination of the functional near-infrared spectroscopy technology and the EEG collection technology, thereby realizing functions like synchronizing or separate collecting of the neural electrical activity and blood oxygen supply information in brain areas.

The electroencephalography (EEG) technology obtains functional information of the brain mainly through measuring changes in electrical activities of the brain neurons, and it has a very high time resolution (ms). Currently, the EEG systems of such companies as NeuroScan, Brain Products GmbH of Germany and EGI of the USA are widely used because they have higher collection accuracy.

The functional Near-infrared spectroscopy (fNIRS) technology is a noninvasive and novel brain function imaging method developed since the 1970s. Its detection principle is to realize detection of functional activities of the cerebral cortex based on the fact that the near-infrared light can well penetrate the brain tissues. Since oxy-hemoglobin and deoxy-hemoglobin have different absorption characteristics of infrared light, the fNIRS measures changes in the intensity of light entering into the cerebral cortex and the intensity of light outcoming from the cerebral cortex tissues after having been scattered and absorbed so as to reflect changes in blood oxygen metabolism in the cerebral cortex. Compared to fMRI, fNIRS has higher time resolution (ms) and is less sensitive to movement; meanwhile, it is light, portable, safe, relatively cheap and can be used for long-time clinical monitoring. Currently, the dominating systems in the market are series ETG-4000 to ETG-7000 systems from Hitachi; systems FOIRE-3000 and OMM-2001 from SHIMADZU Corporation; system CW5 from TechEn (a U.S. company); systems DYNNIRI 932 and Dynot from NIRx medical tech corporation; and system OXYMON MKIII from Artinis (a Dutch company); etc.

Although there have been many devices or system in the market for detecting brain activities, they usually have the following deficiencies:

1) The EEG technology is relatively well developed, but some key technologies still need to be improved, for example, the existence of DC drift during brain electricity collection will easily make the amplifier to work in a saturation state, the existence of common mode interference limits accuracy of the collected data, and the problem of limited frequency bandwidth during brain electricity collection, so a new type full band collection system needs to be developed.

2) Improvements to the NIRS system mostly concern such technical levels as appearance, interface and wireless communication, but no impressive progress has been achieved in fundamental researches on relevant technical problems. Besides, development of the NIRS system in China has been falling behind among nations.

3) Usually, they are all measuring technologies based on a single mode, for example, the EEG only collects electrical activities of the brain neurons, and the fNIRS only collects changes in blood oxygen metabolism in active areas. On the one hand, the manufacturers only focus on manufacturing single-mode measuring systems, and they are not proficient in measurement of other modes; on the other hand, a dual-mode joint collection system has hardware integration cost and design difficulties concerning data synchronous fusion. Up to now, there has not been any photoelectrically synchronous detection device or system at home and abroad yet, nor has any corresponding patent been found.

4) With the progress achieved in science and technology in recent years and out of the urgent clinical needs, there are more and more fundamental researches and application researches on combining the EEG technology and the near-infrared technology, but the current researches are mostly about simply arranging the EEG electrodes and near-infrared optrodes in a cross manner in a certain brain area, and enabling the two independent systems of EEG system and near-infrared system to collect separately through external triggering, and then registering and fusing the two kinds of data in later data analysis. Such a simple design has the following characteristics: first, it does not realize coupling between the electrodes and the optrodes; second, usually the difference of sampling frequencies of the two independent collection systems is great, and they do not achieve synchronous collections of the brain electrical signals and the blood oxygen signals at the same point of the scalp. In addition, in subsequent data analysis process, the time points of the two kinds of signals are usually matched by means of down-sampling or interpolation, so fusion of the EEG data and near-infrared data are not truly realized. Hence, development in fundamental research and clinical application is severely hindered.

SUMMARY OF THE INVENTION

The objects of the present invention are to provide a method and system for brain activity detection to overcome the defects of the prior art, and to realize an integrated collection system that collects electrical activities of brain neurons based on the EEG technology and that synchronously collects changes in blood oxygen metabolism in corresponding brain areas at the same time through the functional near-infrared technology.

To achieve the above objects, the present invention provides a method for brain activity detection, characterized in that said method comprises: performing multi-channel synchronous collections of brain electrical signals and cerebral cortex blood oxygen signals simultaneously, and ensuring synchronicity of the collected signals among channels, and collecting said brain electrical signals and said cerebral cortex blood oxygen signals of all locations at the same time.

Further, multi-channel synchronous collections of brain electrical signals and cerebral cortex blood oxygen signals specifically includes: a central control unit sends synchronous command signals to a blood oxygen detection module and a brain electricity detection module simultaneously, said blood oxygen detection module and said brain electricity detection module simultaneously read, package and label data of their respective modes, and then uploading useful data with identification tags to the central control unit.

Further, said brain electrical signals and cerebral cortex blood oxygen signals are collected at the same location, namely, said brain electrical signals and said cerebral cortex blood oxygen signals are collected at the same point of the scalp.

Further, said central control unit has a corresponding data collection and control software; said central control unit has the capability of downloading light channel frequency and power configuration information, the capability of displaying near-infrared data and brain electrical data in real time, the capability of storing data, and the capability of analyzing and processing data using a data processing algorithm.

To achieve the above-mentioned objects, the present invention provides a system for brain activity detection, said system comprises: a multi-functional joint collection helmet, a functional near-infrared light source emission module, a functional near-infrared detection module, a brain electricity detection module, a central control unit and a host computer; said multi-functional joint collection helmet comprises: a brain electricity electrode, a functional near-infrared light source emission optrode, a functional near-infrared light source receiving optrode, and a flexible material;

said functional near-infrared light source emission module comprises: a control terminal, a modulated wave generating module, an LD drive module, an optical feedback module; and by means of a frequency division multiplexing technique, the light source is modulated by carriers of different frequencies to differentiate light paths of different channels, and said signal is accessed from the multi-functional joint collection helmet through a transmission optical fiber to irradiate the scalp, and after being scattered and absorbed by the brain, the attenuated light signal is processed by the functional near-infrared detection module;

said functional near-infrared detection module comprises: a photoelectric conversion circuit, a demodulating module and a data processing module;

and it is used for detecting weak optical signals of the scalp, said signals being detected by a detection optrode on the multi-functional joint collection helmet and being connected to the functional near-infrared detection module through the transmission optical fiber for such processings as photoelectric conversion, amplification and demodulation;

wherein the demodulation section comprises an analog switch gating circuit, a phase sensitive detection circuit, and a low-pass filtering circuit for identification of the light channels and for analog to digital conversion;

the brain electricity detection module comprises a buffering and amplifying circuit, a signal conditioning module, and a data processing module; and it is used for detecting weak electrical signals of the scalp, said signals being collected by the brain electricity electrode on the multi-functional joint collection helmet and being connected to the brain electricity detection module through a transmission cable for such processings as amplification and modulation;

said central control unit is the core of the photoelectric synchronous brain activity detection system, which is mainly responsible for synchronizing and fusing data flows, sending control commands to each functional module, and uploading data to the host computer.

Further, said functional near-infrared light source module is specifically used for multi-channel parallel emission, wherein the light intensity is emitted with a stable power and is modulated by a carrier.

Further, said functional near-infrared detection module is specifically used for multi-channel parallel detection, wherein the analog switch gating circuit and phase sensitive detection circuit are used for identification and analog-to-digital conversion of different light channels.

Further, said brain electricity detection module employs a buffering and amplifying circuit in which a zero drift operational amplifier and a chopping operational amplifier are combined.

Further, said brain electricity detection module filters noises by sampling common mode noises and by using an adaptive method.

Further, said central control unit is specifically used for sending synchronous command signals to the functional near-infrared detection module and the brain electricity detection module respectively, then the functional near-infrared detection module and the brain electricity detection module simultaneously read, package and label data of their respective modes, and upload useful data with identification tags to said central control unit.

The method and system for brain activity detection according to the present invention have the following advantages:

1. The combination of the two technologies is not simply putting them together. The photoelectric synchronous brain activity detection system overcomes the deficiency in the conventional application in which the EEG electrodes and near-infrared optrodes are simply arranged in a cross manner and the two independent systems are externally triggered to collect separately, it not only optimizes the design of the multi-functional joint collection helmet, but also integrates the signal collection modules of two modes in terms of underlying hardware setting, so it truly realizes synchronization and fusion of optical signals and electrical signals.

2. The combination of the NIRS technology and the EEG collection technology means synchronous collections of optical signals and electrical signals, and can control the interference therebetween to be the minimum.

3. The two kinds of signals have matched time resolutions and good time scale consistency. The whole integrated device can adopt a high sampling frequency, and can realize, in terms of original data collection, synchronous collections of the brain electrical signals and the blood oxygen signals at the same point of the scalp at the same time.

4. The combination of the NIRS and the EEG can enable the device to collect rich and complementary information, besides, the multi-mode information also has explicit physiological significance. By means of the photoelectric synchronous detection system, a correspondence between the blood oxygen signals and the neuron activities can be established while taking functional areas as the units.

5. Having the advantages of being portable, low-cost and capable of long-time clinical application.

6. Tracking and analysis of neuron activities and changes in blood oxygen concentration can be realized synchronously, and data collection and analysis can be performed for special groups like infants.

DETAILED DESCRIPTION OF THE INVENTION

The technical solution of the present invention will be described in further detail below in conjunction with the drawings and embodiments.

The present invention provides a method for brain activity detection, which mainly comprises: performing multi-channel synchronous collections of brain electrical signals and cerebral cortex blood oxygen signals simultaneously, and ensuring synchronicity of the collected signals among channels, and collecting brain electrical signals and cerebral cortex blood oxygen signals of all locations at the same time.

The combination of the NIRS technology and the EEG collection technology means synchronous collections of optical signals and electrical signals, and can control the interference to be the minimum. Besides, the two kinds of signals have matched time resolutions and good time scale consistency.

The multi-channel synchronous collections of brain electrical signals and cerebral cortex blood oxygen signals specifically includes: a central control unit sends synchronous command signals to a blood oxygen detection module and a brain electricity detection module simultaneously, said blood oxygen detection module and said brain electricity detection module simultaneously read, package and label data of their respective modes, and then upload useful data with identification tags to the central control unit.

Collecting the brain electrical signals and the blood oxygen signals of the cerebral cortex at the same location means that at the same point of the scalp, both the brain electrical signals and the blood oxygen signals of the cerebral cortex are collected.

The method can use the NIRS and the EGG in combination and can establish a correspondence between the blood oxygen signals and the neuron activities by means of the photoelectric synchronous detection system while taking functional areas as the units; it can track and analyze neuron activities and changes in blood oxygen concentration synchronously, and can collect data from special patients like infants to aid in analysis of their brain function activities; and it can study and analyze other mental illness.

Figure 1:
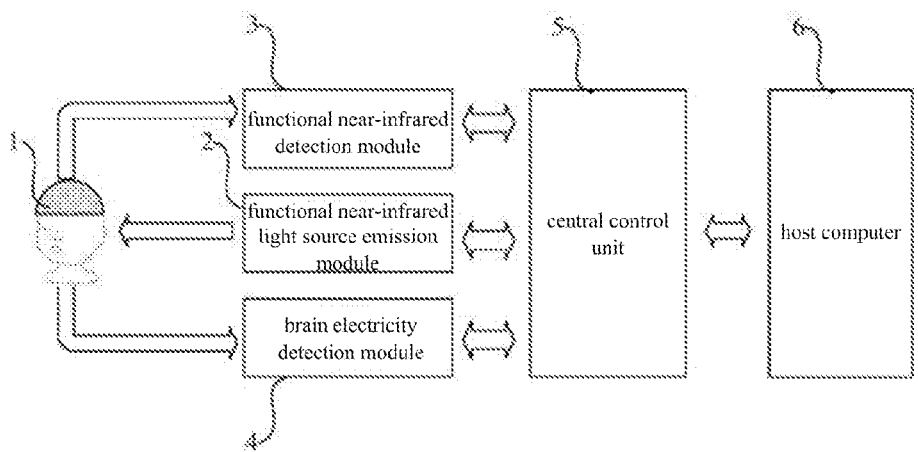
FIG. 1 is a schematic drawing of the system for brain activity detection according to the present invention.

FIG. 1 is a schematic drawing of the system for brain activity detection according to the present invention. As shown in the figure, the present invention specifically comprises: a multi-functional joint collection helmet 1, a functional near-infrared light source emission module 2, a functional near-infrared detection module 3, a brain electricity detection module 4, a central control unit 5 and a host computer 6. The multi-functional joint collection helmet 1 is used for arranging the brain electricity electrodes and the functional near-infrared optrodes in a cross manner; the functional near-infrared light source emission module 2 is used for controlling stable emission of the near-infrared light source and for connecting signals to the multi-functional joint collection helmet 1 through an optical fiber; the functional near-infrared detection module 3 is used for detecting weak optical signals of the scalp and is connected to the multi-functional joint collection helmet 1 through an optical fiber; the brain electricity detection module 4 is used for detecting weak electrical signals of the scalp and is connected to the multi-functional joint collection helmet 1 through a transmission cable; the central control unit 5 is used for realizing coordinated control of the system, including synchronizing and fusing of data flows, sending control commands to each functional module, uploading data to the host computer 6, etc.; and the host computer 6 functions as a human machine interface and is used for display and processing data in real time, downloading control commands, and so on.

As a preferred embodiment, the multi-functional joint collection helmet 1 comprises: a brain electricity electrode, a functional near-infrared light source emission optrode, and a functional near-infrared light source receiving optrode. As a more preferred embodiment, the multi-functional joint collection helmet can use a flexible material that covers the scalp so as to increase the degree of comfort of the tested person. As a more preferred embodiment, the multi-functional joint collection helmet can have a brain electricity electrode base, a functional near-infrared emission optrode base, and a functional near-infrared receiving optrode base arranged on the flexible material that covers the scalp. The base and the electrode/optrode are designed to be separated to enable easy plug.

As a preferred embodiment, the functional near-infrared light source emission module 2 comprises: a control terminal, a modulated wave generating module, a light emitting diode (LED or LD) drive module, and an optical feedback module. The functional near-infrared light source emission module uses the frequency division multiplexing technique, and the light source is modulated by carriers of different frequencies to differentiate light paths of different channels, and said signal is accessed from the multi-functional joint collection helmet through a transmission optical fiber to irradiate the scalp, and after being scattered and absorbed by the brain, the attenuated light signal is processed by the functional near-infrared detection module.

As a preferred embodiment, the functional near-infrared detection module 3 comprises: a photoelectric conversion circuit, a demodulating module and a data processing module; and said functional near-infrared detection module is used for detecting weak optical signals of the scalp, said signals being detected by a detection optrode on the multi-functional joint collection helmet and being connected to the functional near-infrared detection module through the transmission optical fiber for such processings as photoelectric conversion, amplification and demodulation; wherein the demodulation section comprises an analog switch gating circuit, a phase sensitive detection circuit, and a low-pass filtering circuit for identification of the light channels and for analog to digital conversion.

As a preferred embodiment, the brain electricity detection module 4 comprises a buffering and amplifying circuit, a signal conditioning module, and a data processing module; and said brain electricity detection module is used for detecting weak electrical signals of the scalp, said signals being collected by a brain electricity electrode on the multi-functional joint collection helmet and being connected to the brain electricity detection module through the transmission cable for such processings as amplification and conditioning.

The central control unit 5 is the core of the photoelectric synchronous brain activity detection system, which is mainly responsible for synchronizing and combining data flows, sending control commands to each functional module, and uploading data to the host computer.

On the one hand, optical signal detection is carried out. First, the host computer configures the emission frequency and emission power of the light source, then said configuration information is downloaded to the central control unit which writes the emission frequency and emission power of the light source to a controller of the functional near-infrared emission module, thereby generating modulated waves of the near-infrared optical signals. Optical signals generated by the functional near-infrared light source emission module are connected to the multi-functional joint collection helmet through a transmission optical fiber, and the near-infrared light is scattered and absorbed by the brain, then the attenuated weak optical signals are transmitted to the functional near-infrared detection module by the receiving optrode of the multi-functional joint collection helmet through an optical fiber, and said detection module performs photoelectric conversion, demodulation and corresponding data processing for the detected weak optical signals, and then uploads them to the central control unit. On the other hand, brain electrical signal detection is carried out. The weak electrical signals of the scalp are collected by the brain electricity electrode of the multi-functional joint collection helmet, and are transmitted through the transmission cable to the brain electricity detection module for processings like buffering and amplifying, etc., then they are uploaded to the central control unit. Synchronization of data flows of the optical signals and brain electrical signals is mainly coordinated and achieved by the central control unit.

Figure 2A:
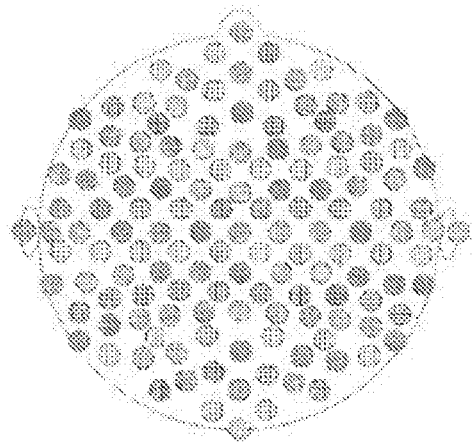
FIGS. 2A and 2B are exemplary diagrams of the multi-functional joint collection helmet in the system for brain activity detection according to the present invention.
Figure 2B:
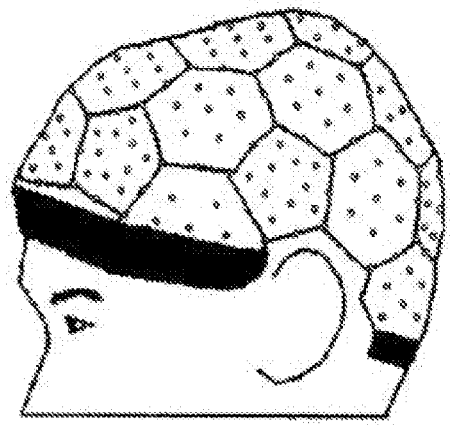

FIGS. 2A and 2B are exemplary diagrams of the multi-functional joint collection helmet in the system for brain activity detection according to the present invention. The multi-functional joint collection helmet mainly includes a flexible material covering the scalp, a brain electricity electrode base, a functional near-infrared emission optrode base, a functional near-infrared receiving optrode base, a brain electricity electrode, a functional near-infrared emission optrode and a functional near-infrared receiving optrode. Wherein, the brain electricity electrode and the functional near-infrared light optrode are arranged in a cross manner. The bases and the electrode/optrode are designed to be separated to enable easy plug.

Figure 3:
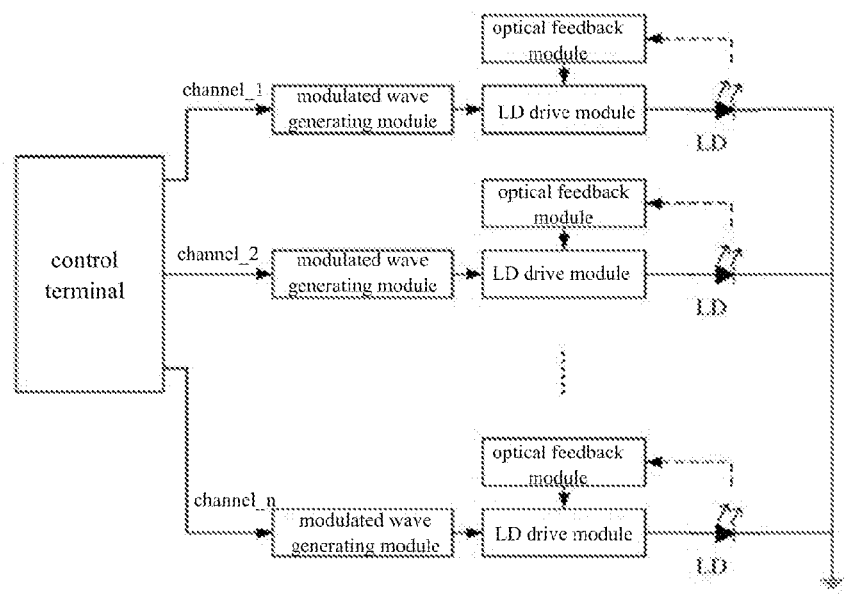
FIG. 3 is a principle diagram of the functional near-infrared light source emission module in the system for brain activity detection according to the present invention.

FIG. 3 is a principle diagram of the functional near-infrared light source emission module in the system for brain activity detection according to the present invention. Said module mainly comprises a control terminal, a modulated wave generating module, an LD drive module and an optical feedback module. First, the control terminal writes control commands and sends them to the modulated wave generating module to generate modulated wave signals having corresponding emission frequency and power so as to control the LD to flicker at a fixed frequency. During operation of the LD, the LD drive module and the optical feedback module work together to make it output carrier optical signals having stable power. The optical feedback module uses a photoelectric conversion diode to feed back the unstable fluctuation of the received LD power, and at the same time suppresses the power fluctuation in combination with the LD drive module, and a multi-channel modulated wave signal generating module and LD module can be provided to realize control and emission of multi-channel parallel carrier light. Stably emitted optical signals are connected to the multi-functional joint collection helmet through the transmission optical fiber, and the emitted light penetrates the brain and is scattered and absorbed, then weak optical signals carrying blood oxygen information are output.

Figure 4:
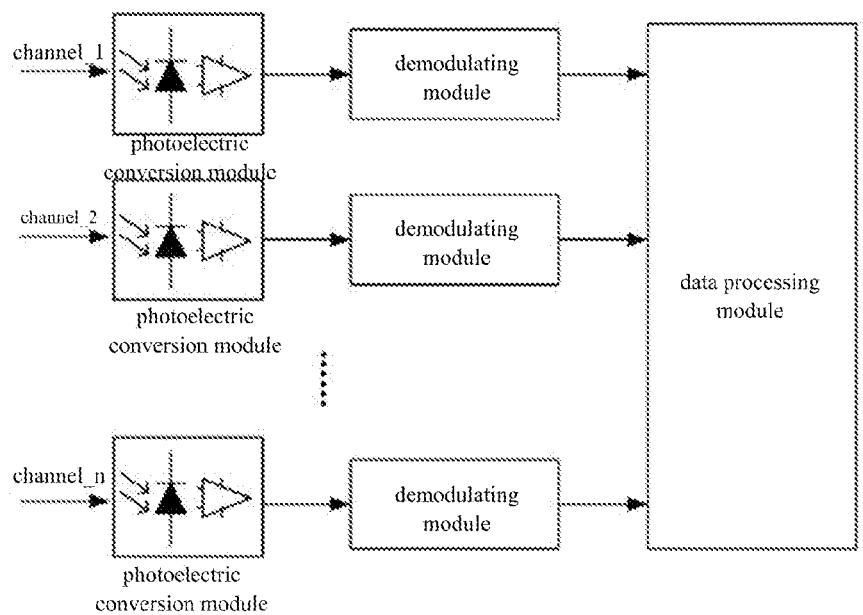
FIG. 4 is a principle diagram of the functional near-infrared detection module in the system for brain activity detection according to the present invention.

FIG. 4 is a principle diagram of the functional near-infrared detection module in the system for brain activity detection according to the present invention. Said module comprises a photoelectric conversion module, a demodulating module and a data processing module. Weak optical signals at the surface of the scalp are collected by the near-infrared receiving optrode of the multi-functional joint collection helmet and are then transmitted through the transmission optical fiber to the functional near-infrared detection module for photoelectric conversion, amplification, demodulation, and corresponding data processing. Wherein the core component used in the photoelectric conversion module is an APD which converts the transmitted optical signals carrying blood oxygen information into electrical signals and performs a blocking processing to said electrical signals to eliminate influence of the ambient light, then it delivers the electrical signals to a channel demodulation module for demodulation. The demodulation module mainly adopts a phase-lock amplifier to demodulate and subsequently process useful signals of each channel.

Figure 5:
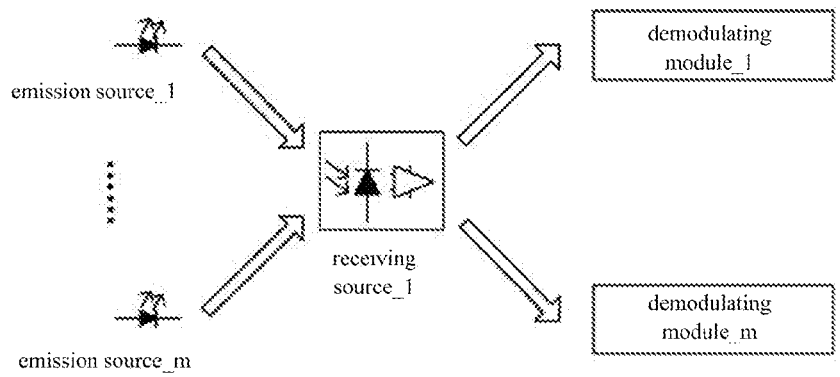
FIG. 5 is one of the schematic drawings of the functional near-infrared emission optrode and receiving optrode in the system for brain activity detection according to the present invention.
Figure 6:
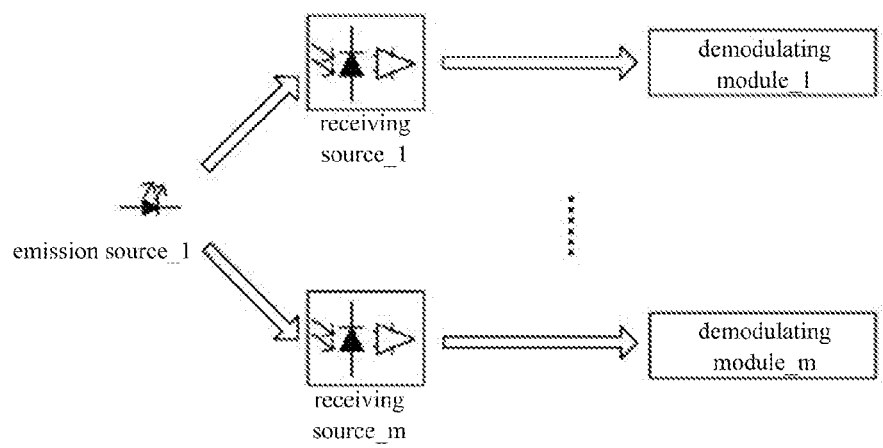
FIG. 6 is another one of the schematic drawings of the functional near-infrared emission optrode and receiving optrode in the system for brain activity detection according to the present invention.

FIG. 5 is one of the schematic drawings of the functional near-infrared emission optrode and receiving optrode in the system for brain activity detection according to the present invention. In the figure, multiple emission optrodes correspond to one receiving optrode. FIG. 6 is another one of the schematic drawings of the functional near-infrared emission optrode and receiving optrode in the system for brain activity detection according to the present invention. In the figure, one emission optrode corresponds to multiple receiving optrodes.

In order to increase utilization rate of the light source, the present invention uses an analog switch gating circuit to realize independent gating of multiple light channels. The ratio of the near-infrared emission optrode and the receiving optrode can be one-to-one, one-to-many, many-to-one, and has simple structure and flexible functions, and the manufacturing cost can also be greatly reduced.

Figure 7:
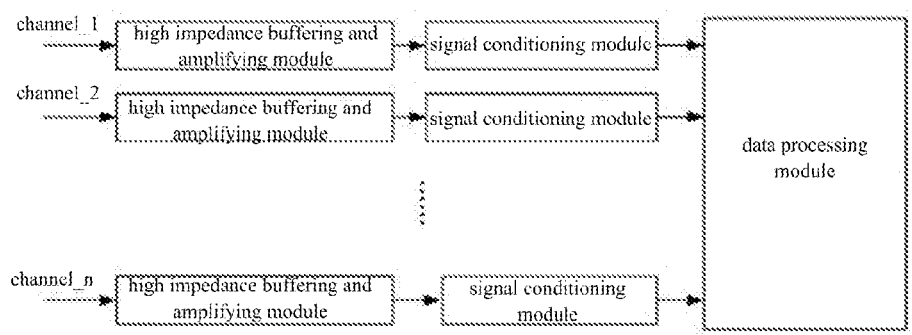
FIG. 7 is a principle diagram of the brain electricity detection module in the system for brain activity detection according to the present invention.

FIG. 7 is a principle diagram of the brain electricity detection module in the system for brain activity detection according to the present invention. Said module mainly comprises a high impedance buffering and amplifying module, a signal conditioning module, and a data processing module. The weak electrical signals at the scalp surface are collected by the brain electricity electrode of the multi-functional joint collection helmet and are connected through the transmission cable to the brain electricity detection module for buffering, amplifying and other processings. Wherein, the high impedance buffering and amplifying circuit uses a zero drift operational amplifier and a chopping operational amplifier in combination to reduce DC drift of the amplifier, meanwhile, DC information is retained by means of sampling, then in a back end signal conditioning module, the DC is canceled to obtain AC signals. The retained DC signals and the obtained AC signals are respectively amplified by different amplification factors using different amplifying circuits, then the AC and DC signals are integrated at a digital end to finally obtain the actual brain electrical signals. With respect to the problem of common mode interference, noises are filtered through a digital signal processing algorithm to increase accuracy of the collected data, thereby increasing the common mode rejection ratio of the amplifier.

Figure 8:
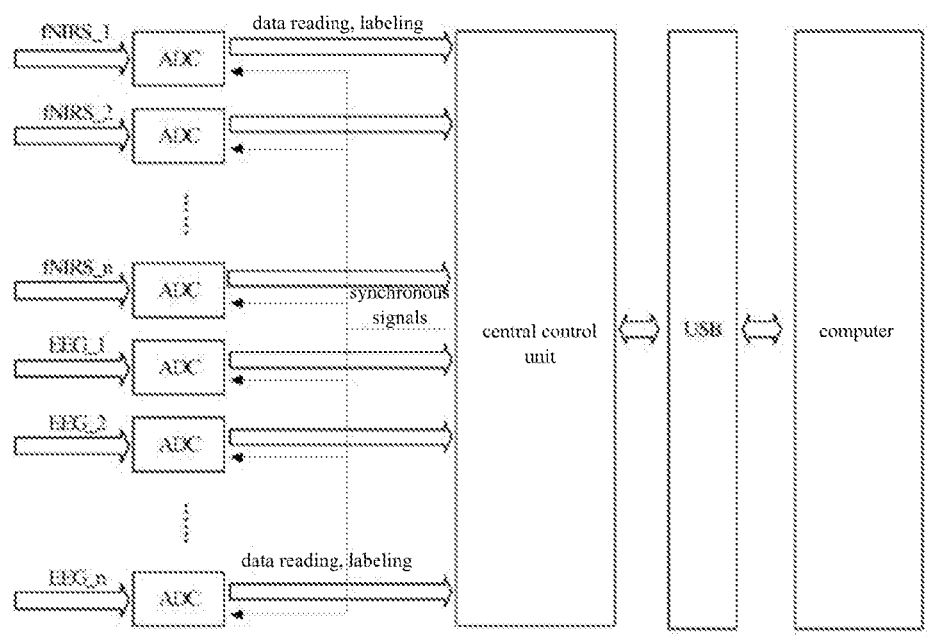
FIG. 8 is a principle diagram of data flow synchronization in the system for brain activity detection according to the present invention.

FIG. 8 is a principle diagram of data flow synchronization in the system for brain activity detection according to the present invention. When the photoelectric synchronous brain activity detection system is operating in a synchronous collecting mode, data flows of the functional near-infrared unit and the brain electricity unit need to be synchronized. The central control unit is the core of the whole photoelectric synchronous brain activity detection system, and it is also the coordination center controlling synchronization of the data flows. First, the central control unit sends synchronous signals to a corresponding near-infrared ADC module and a brain electricity ADC module, then the ADC modules read, package and label their respective near-infrared data and brain electricity data, and then upload useful data with identification tags to the central control unit for subsequent processing. Said method of synchronization guarantees time accuracy of synchronous collections of the near-infrared data and brain electricity data, thus truly realizes synchronous collections of optical signals and electrical signals.

Because of adopting the above-described technical solution, the present invention has the following advantages:

1. The system adopts a modular design, each of the modules has a more clearly specified function and a reasonable structure, and is easily controllable and stable and reliable, and has high degree of integration and expansibility.
2. By effectively fusing the fNIRS technology and the EEG collection technology, integration of the three functions of near-infrared spectrometer, electroencephalograph and fusion device of near-infrared spectrum and electroencephalograph can be realized on one instrument, thereby achieving functions like synchronizing or separate collecting of the neural electrical activity and blood oxygen supply information in brain areas.
3. The combination of the two technologies is not simply putting them together. The photoelectric synchronous brain activity detection system overcomes the deficiency in the conventional application in which the EEG electrodes and near-infrared optrodes are simply arranged in a cross manner and the two independent systems are externally triggered to collect separately, it not only optimizes the design of the multi-functional joint collection helmet, but also integrates the signal collection modules of two modes in terms of underlying hardware setting, so it truly realizes synchronization and fusion both of optical signals and electrical signals.
4. The two kinds of signals have matched time resolutions and good time scale consistency. The whole integrated device can adopt a high sampling frequency, and can realize, in terms of original data collection, synchronous collections of the brain electrical signals and the blood oxygen signals at the same point of the scalp at the same time.
5. Synchronization of data flows in the photoelectric synchronous brain activity detection system is coordinated and controlled by the central control unit. As the core component of the whole photoelectric synchronous brain activity detection system, the central control unit sends a synchronous start signal to the functional near-infrared detection module and the brain electricity detection module, then said dual-mode detection modules read, package and label their respective data, and then upload multi-channel useful data with identification tags to the central control unit for subsequent processing. Said synchronization strategy ensures time accuracy and synchronicity of the photoelectric signals.
6. The multi-functional joint collection helmet has a flexible design, wherein the brain electricity electrodes and the functional near-infrared optrodes are arranged in a cross manner, and corresponding bases are provided to enable easy plug.
7. The functional near-infrared light source emission module adopts the frequency division multiplexing technique to overcome defects of the conventional time division multiplexing and to ensure that the system has a high time accuracy, thus realizing parallel and stable emission of multiple light channels. A multi-wavelength LD light source is employed, which can reduce the manufacturing cost while overcoming the defects that laser light source has high cost and limited range of wavelength, and that a light source coupler is needed to couple two laser light sources together so as to meet the requirement of one collection channel.
8. An analog switch gating circuit is used to realize independent gating of multiple light channels. The ratio of the near-infrared emission optrode and the receiving optrode can be one-to-one, one-to-many, many-to-one, so that the light source utilization rate of the entire system is greatly increased.
9. The functional near-infrared detection module uses an avalanche photodiode (APD), which, compared to conventional photomultiplier tube, has a much lower manufacturing cost and wider wavelength application range. In addition, the photomultiplier tube has such disadvantages as being unstable, having poor resistance to mechanical impact and having a "fatigue" phenomenon, so using the APD can enable the system to work in a more continuous and stable manner.
10. The brain electricity detection module employs a buffering and amplifying circuit in which a zero drift operational amplifier and a chopping operational amplifier are combined, thus greatly reducing DC drift of the amplifier. With respect to the problem of common mode interference, by sampling the common mode noises and using an adaptive method to filter noises, data collection accuracy is improved.
11. The design of the multi-functional joint collection helmet, the modularized integration of the functional near-infrared system and the brain electricity system as well as the design of the method for synchronizing data flows have substantively fused and integrated the two collection technologies, thus truly realized photoelectric synchronization.

Those skilled in the art shall be aware that the exemplary units and algorithm steps described in conjunction with the embodiments disclosed herein can be realized by electronic hardware, computer software or a combination thereof, and in order to clearly illustrate the interchangeability between the hardware and software, the exemplary components and steps have been generally described above in terms of the functions thereof. As for whether said functions should be achieved by hardware or by software, it depends on the specific application and restrictions of design of the technical solution. Those skilled in the art can use a different method for each specific application so as to achieve the described functions, but such implementation shall not be considered as going beyond the scope of the present invention.

The steps of method or algorithm described in conjunction with the embodiments disclosed herein can be carried out by hardware, software modules executed by a processor or by a combination thereof. The software modules can be disposed in a random access memory (RAM), a memory, a read-only memory (ROM), an electrically-programmable ROM, an electrically erasable programmable ROM, a register, a hard disc, a removable disc, a CD-ROM or any other form of storage medium known in the art.

The above-described specific embodiment describes in detail the object, technical solution and advantageous effect of the present invention. But it shall be appreciated that all the above described are merely specific embodiments of the present invention, which do not intend to limit the protection scope of the invention. Any modification, equivalent substitution and improvement made under the spirit and principle of the present invention shall fall within the protection scope of the present invention.

What is claimed is:

1. A system for detecting brain activity, comprising:
   a joint collection helmet,
   a near-infrared light source emission module,
   a near-infrared detection module,
   a brain electricity detection module,
   a central control unit and a host computer;
   said joint collection helmet comprising:
      a brain electricity electrode,
      a near-infrared light source emission optrode,
      a near-infrared light source receiving optrode, and
      a flexible material;
   said near-infrared light source emission module comprising:
      a control terminal,
      a modulated wave generating module,
      an LED drive module,
      an optical feedback module; and
      using a frequency division multiplexing technique, the light source is modulated by carriers of different frequencies to differentiate light signals of different channels, and said light signals are accessed from the joint collection helmet through a fiber optic transmission cable to irradiate a scalp, and after being scattered and absorbed by the brain, the light signals are processed by the near-infrared detection module;
   said near-infrared detection module comprising:
      an avalanche photodiode,
      a demodulating module, and
      a computer processor;
   wherein the near-infrared detection module detects optical signals of the scalp,
      wherein said optical signals are detected by the receiving optrode on the joint collection helmet which is connected to the near-infrared detection module through fiber optic transmission cable to one of the set containing: avalanche photodiode, an amplifier, cation and the demodulating module;
      wherein the demodulating module comprises:
         an analog switch gating circuit,
         a phase sensitive detection circuit, and
         a low-pass filtering circuit for identification of the light channels and for analog to digital conversion;
   wherein the brain electricity detection module comprises:
      a buffering and amplifying circuit,
      a DC filtering circuit;
      a computer processor; and
      wherein the brain electricity detection module is used for detecting electrical signals of the scalp,
      wherein the electric signals are collected by the brain electricity electrode on the joint collection helmet which is connected to the brain electricity detection module through a transmission cable;
      and wherein said central control unit is the core of a photoelectric synchronous brain activity detection system, which is responsible for synchronizing and fusing data flows, sending control commands to each module, and uploading data to the host computer.

2. The system according to claim 1, wherein the near-infrared light source module is used for multi-channel parallel emission, and wherein the light intensity is emitted with a stable power and is modulated by a carrier.

3. The system according to claim 1, wherein the near-infrared detection module is used for multi-channel parallel detection, and wherein the analog switch gating circuit and phase sensitive detection circuit are used for identification and analog-to-digital conversion of different light channels.

4. The system according to claim 1, wherein the brain electricity detection module employs the buffering and amplifying circuit in which a zero drift operational amplifier and a chopping operational amplifier are combined.

5. The system according to claim 1, wherein the brain electricity detection module filters noises by sampling common mode noises and by using an adaptive method.

6. The system according to claim 1, wherein the central control unit is used for sending synchronous command signals to the near-infrared detection module and the brain electricity detection module respectively, and then the near-infrared detection module and the brain electricity detection module simultaneously read, package and label data of their respective modes, and upload data with identification tags to said central control unit.

* * * * *